(12) United States Patent
Kutose et al.

(10) Patent No.: US 8,962,849 B2
(45) Date of Patent: Feb. 24, 2015

(54) NITROGEN-CONTAINING HETEROCYCLIC COMPOUND AND METHOD FOR PRODUCING SAME

(71) Applicant: Nippon Soda Co., Ltd., Tokyo (JP)

(72) Inventors: Koichi Kutose, Takaoka (JP); Hiroki Inoue, Takaoka (JP); Shiro Tsubokura, Takaoka (JP)

(73) Assignee: Nippon Soda Co., Ltd., Tokyo (JP)

( * ) Notice: Subject to any disclaimer, the term of this patent is extended or adjusted under 35 U.S.C. 154(b) by 0 days.

(21) Appl. No.: 14/175,879

(22) Filed: Feb. 7, 2014

(65) Prior Publication Data
US 2014/0171651 A1    Jun. 19, 2014

Related U.S. Application Data

(62) Division of application No. 13/638,700, filed as application No. PCT/JP2011/057521 on Mar. 28, 2011, now Pat. No. 8,703,959.

(30) Foreign Application Priority Data

| Apr. 6, 2010 | (JP) | 2010-087915 |
| Apr. 6, 2010 | (JP) | 2010-087916 |
| May 7, 2010 | (JP) | 2010-107195 |

(51) Int. Cl.
| C07D 213/00 | (2006.01) |
| C07D 213/89 | (2006.01) |
| C07D 213/75 | (2006.01) |

(52) U.S. Cl.
CPC ............ *C07D 213/89* (2013.01); *C07D 213/75* (2013.01)
USPC ........................................................ 546/309

(58) Field of Classification Search
None
See application file for complete search history.

(56) References Cited

U.S. PATENT DOCUMENTS

| 3,047,579 A | 7/1962 | Witman |
| 3,907,798 A | 9/1975 | Lesher |
| 4,211,873 A | 7/1980 | Pews et al. |
| 4,731,482 A | 3/1988 | Venturello et al. |
| 5,872,136 A | 2/1999 | Anthony et al. |
| 7,678,815 B2 | 3/2010 | Buettelmann et al. |

FOREIGN PATENT DOCUMENTS

| CN | 1121074 | 4/1996 |
| CN | 1347881 | 5/2002 |
| CN | 1982297 | 6/2007 |
| JP | 62-1412136 | 6/1987 |
| JP | 01-224364 | 9/1989 |
| JP | 07-252226 | 10/1995 |
| JP | 07-330764 | 12/1995 |
| JP | 08-506107 | 7/1996 |
| JP | 10-324678 | 12/1998 |
| JP | 2000-502356 | 2/2000 |
| JP | 2000-507590 | 6/2000 |
| JP | 2003-231677 | 8/2003 |
| JP | 2005-255560 | 9/2005 |
| JP | 2008-526909 | 7/2008 |
| JP | 2008-531618 | 8/2008 |
| KR | 10-2005-0025453 | 3/2005 |
| SU | 943235 A1 | 7/1982 |
| WO | 2008/006873 | 1/2008 |
| WO | 2008-070014 | 6/2008 |
| WO | 2009/115557 | 9/2009 |

OTHER PUBLICATIONS

Narendar, P. Synth. Comm 2004 vol. 34 pp. 1097-1103.*
Barnes, John H., et al., "The Preparation of 4- and 6-Chloro-2-Chloromethylpyridine", Tetrahedron, 1982, vol. 38, No. 22, pp. 3277-3280.
Narendar, P., et al., "Facile and Selective Synthesis of Chloromethylpyridines and Chloropyridines Using Diphosgene/Triphosgene", Synthetic Communications, 2004, vol. 34, No. 6, pp. 1097-1103.
Goswami, Shyamaprasad, et al., "Directed H-bonding inhibition in molecular recognition: an NMR case study of the H-bonding of a dicarboxylic acid with a new mixed diamide receptor having one adjacent pyridine-N-oxide", Tetrahedron Letters, 2005, vol. 46, pp. 1315-1318.
Database CASREACT on STN, AN123: 32933, Sinha, N., et al., "Rearrangement of heteroaromatic N-oxides. A new synthesis of (chloromethyl) quinoline", Journal of the Indian Chemical Society, 1994, vol. 71, No. 12, pp. 763-764, Abstract.

(Continued)

*Primary Examiner* — Heidi Reese
(74) *Attorney, Agent, or Firm* — Kenyon & Kenyon, LLP

(57) ABSTRACT

There are provided a nitrogen-containing heterocyclic compound such as a substituted amino-pyridine-N-oxide compound represented by formula (1), which is useful as a synthetic intermediate for an agrochemical and the like; and a method for producing the nitrogen-containing heterocyclic compound. (In formula (1), $R^1$ and $R^2$ each represents a hydrogen atom or an unsubstituted or substituted alkyl group; $R^3$ represents a hydrogen atom, an unsubstituted or substituted alkylcarbonyl group or the like; $R^4$ represents an unsubstituted or substituted alkylcarbonyl group, an unsubstituted or substituted arylcarbonyl group or the like; A represents a hydroxyl group, a thiol group or the like; m represents any one of integers of 1 to 4; k represents any one of integers of 0 to 3; and k+m≤4.).

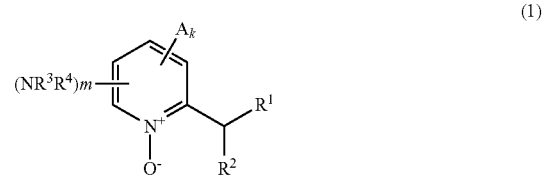

(1)

11 Claims, No Drawings

(56) References Cited

OTHER PUBLICATIONS

Database CASREACT on STN, AN119: 8777, Jae Keun, L., et al., "1,2,4-Triazine IV: conversion of 1,2,4-triazine N4-oxides to chloro- and chloromethyl-1,2,4-triazines with phosphorus oxychloride", Journal of the Korean Chemical Society, 1993, vol. 37, No. 1, pp. 162-164, Abstract.

Database CASREACT on STN, AN148: 585682, Nan, M., et al., "Improvement on the synthesis of 2-chloromethyl-4-methoxy-3,5-dimethylpyridine", Hecheng Huaxue, 2007, vol. 15, No. 3, pp. 385-387, Abstract.

Brieaddy, Lawrence E., et al., "Synthesis of bridged analogs of epibatidine. 3-Chloro-5,7,8,9,9a,10-hexahydro-7,10-methanopyrrolo[1,2-*b*]-2,6-naphthyridine and 2-chloro-5,5a,6,7,8,10-hexahydro-5,8-methanopyrrolo[2,1-*b*]-1,7-naphthyridine", Tetrahedron Letters, 2001, vol. 42, pp. 3795-3797.

International Search Report issued for PCT/JP2011/057521, dated Apr. 26, 2011, 10 pages (with English translation).

EP Communication including Supplementary European Search Report from EP Appln. No. 11765468.1, Jul. 18, 2013, 12 pages.

Office Action issued in CN Application No. 201180017458.2, Aug. 6, 2013, 30 pages (with EN translation).

Non-Final Office Action (Restriction Requirement) mailed on May 14, 2013, issued in the parent U.S. Appl. No. 13/638,700, 7 pages.

Non-Final Office Action (Restriction Requirement) mailed on Aug. 27, 2013, issued in the parent U.S. Appl. No. 13/638,700, 7 pages.

EP Communication including European Search Report from EP Appln. No. 14154040.1, dated Mar. 18, 2014, 5 pages.

Non-Final Office Action mailed on Apr. 3, 2014, issued in the U.S. Appl. No. 14/175,535, 7 pages.

Adams et al., "2-Aminopyridine 1-Oxides", J. Amer. Chem. Soc., 1954, vol. 76, pp. 2785-2786.

Bruni et al., "The reaction of 1,1,2,2-Ethenetetracarbonitrite (TCNE) With Aminopyridines: Salts and Charge Transfer Complex Formation", CAPLUS 1989: 632530, 2 pages.

Final Office Action mailed on Jul. 16, 2014, issued in the U.S. Appl. No. 14/175,535, 6 pages.

Gardner et al., "N-Oxides and Related Compounds. V. The Tautomerism of 2- and 4-amino- and -hydroxy pyridine 1-oxide", Journal of the Chemical Society (1957), Univ. Oxford, UK, 1958:25529 CAPLUS, 2 pages.

Notice of Allowance issued in RU Appln. No. 2012142172, dated Aug. 7, 2014, 14 pages (with translation).

Office Action issued in U.S. Appl. No. 14/175,535, dated Sep. 24, 2014, 5 pages.

Childress et al., "Sulfapyridine-1-oxides", J. Org. Chem., Jan. 1958, vol. 23, pp. 67-69.

Childress et al., "Sulfapyridine-1-oxides", J. Org. Chern., Jan. 1958, vol. 23, pp. 67-69.

Notice of Allowance issued in U.S. Appl. No. 14/175,958, dated Nov. 25, 2014, 35 pages.

Felton et al., "A Wavelength and Lifetime Responsive Cryptate-Containing Fluorescent Probe for Zinc Ions in Water", Chem. Commun., 2008, vol. 46, pp. 6185-6187.

\* cited by examiner

NITROGEN-CONTAINING HETEROCYCLIC COMPOUND AND METHOD FOR PRODUCING SAME

CROSS-REFERENCE TO RELATED APPLICATIONS

This application is a Divisional application of U.S. application Ser. No. 13/638,700, filed on Oct. 1,2012, which is a national phase application of PCT/JP2011/057521 filed on Mar. 28, 2011, which claims priority under 35 U.S.C. 119 to Japanese Patent Application No. 2010-087915, filed Apr. 6, 2010, Japanese Patent Application No. 2010-087916, filed Apr. 6, 2010, and Japanese Patent Application No. 2010-107195, filed May. 7, 2010, the contents of each are hereby incorporated by reference.

TECHNICAL FIELD

The present invention relates to a nitrogen-containing heterocyclic compound and a method for producing the same. More specifically, the present invention relates to: (1) a substituted amino-pyridine-N-oxide derivative which is useful as a synthetic intermediate of agricultural chemicals or the like; (2) a method for producing a substituted amino-6-methylpyridine-N-oxide derivative; and (3) a method for producing a haloalkyl, nitrogen-containing heterocyclic derivative.

BACKGROUND ART

A 2-substituted amino-6-methylpyridine-N-oxide derivative is useful as an intermediate for the synthesis of chemical substances for pharmaceuticals and agrochemicals such as the tetrazolyloxime derivative disclosed in Patent Document 1 since the halogenation or the like of a methyl group at position 6 is easy.

In general, pyridine-N-oxide derivatives can be obtained by the oxidation of pyridine derivatives. For example, in Patent Document 2, a method for producing 2-chloro-pyridine-N-oxide by the oxidation of 2-chloro-pyridine using hydrogen peroxide in the presence of a catalyst represented by $Y[PW_2O_{13}(OH)]$ (in which Y represents a hydrogen atom, alkyl or ammonium) has been disclosed.

In addition, with respect to the reaction of pyridine-N-oxide derivatives, as a method for introducing a halogen into the methyl group of 2-picoline derivatives, for example, it has been reported in Non-Patent Document 1 that 6-chloro-2-chloromethyl pyridine can be produced by rearranging 6-chloro-2-methylpyridine-N-oxide with acetic anhydride to introduce oxygen to the methyl group, followed by the action of thionyl chloride thereon.

In Non-Patent Document 2, a halogenation method by reacting triphosgene or diphosgene with 2-picoline-N-oxide in the presence of di-1-propylamine or triethylamine has been reported.

In addition, in Patent Document 3, a method to synthesize 2-chloro-5-methylpyridine from 3-methylpyridine-1-oxide has been shown. According to Patent Document 3, it has been reported that a desired product can be obtained by the method through a rearrangement reaction using trimethylamine and phosgene to convert the 2nd position of the pyridine ring to trimethylammonium, followed by chlorination thereof.

CITATION LIST

Patent Document

Patent Document 1: WO2008/006873
Patent Document 2: KR-A-10-2005-0025453
Patent Document 3: Japanese Unexamined Patent Application, First Publication No. Hei 7-252226
Patent Document 4: Japanese Unexamined Patent Application, First Publication No. Sho 62-142136

Non-Patent Document

Non-Patent Document 1: Barnes, J. H. et al., Tetrahedron 38 (22), 3277-3280, 1982
Non-Patent Document 2: Narendar P. et al., Synthetic Communications 34 (6), 1097-1103, 2004

SUMMARY OF INVENTION

Technical Problem

The inventors of the present invention have an object of providing a method for producing a substituted amino-pyridine-N-oxide derivative represented by the formula (1), in particular, a substituted amino-6-alkyl-pyridine-N-oxide derivative, which is highly selective, easy to separate the catalyst, and also useful as an intermediate for the synthesis of agricultural chemicals and the like. In addition, another object is to provide a highly selective and also high yield method for producing a haloalkyl, nitrogen-containing heterocyclic derivative represented by the formula (5) which is also useful as an intermediate for the synthesis of pharmaceuticals and agrochemicals.

Solution to Problem

As a result of intensive and extensive studies in order to achieve the above objects, the inventors of the present invention found that, among the tungstophosphoric acid salts represented by $Q_3[PW_4O_{24}]$ that are known as a catalyst for the epoxidation reaction in Patent Document 4 or the like, by using those in which Q represents a quaternary nitrogen cation as a catalyst, a substituted amino-6-methylpyridine-N-oxide derivative can be obtained with high selectivity through an oxidation reaction of a substituted amino-6-methylpyridine derivative with a peroxide, and that the catalyst can be easily separated after the completion of the reaction.

In addition, the inventors of the present invention have found that a compound represented by formula (5) can be produced in high yield and also with high selectivity by reacting a compound represented by formula (4) with a halogenating agent such as thionyl chloride, thionyl bromide or sulfuryl chloride. Further, the inventors of the present invention have also discovered that a compound represented by formula (5) can be produced in high yield and also with high selectivity by reacting a compound represented by formula (4) with a halogenating agent such as phosgene, diphosgene, triphosgene or phosphorus oxychloride in the presence of a source of halogen ions which is soluble in an organic solvent.

The present invention has been completed by further studies based on these findings.

That is, the present invention includes the following aspects.

[1] A substituted amino-pyridine-N-oxide compound represented by formula (1):

[Chemical Formula 1]

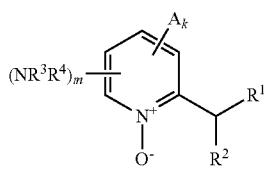

(1)

(in the formula (1), each of $R^1$ and $R^2$ independently represents a hydrogen atom, or an unsubstituted or substituted alkyl group, and $R^1$ and $R^2$ may form a ring together, $R^3$ represents a hydrogen atom, an unsubstituted or substituted alkylcarbonyl group, an unsubstituted or substituted arylcarbonyl group, or an unsubstituted or substituted alkoxycarbonyl group, $R^4$ represents an unsubstituted or substituted alkylcarbonyl group, an unsubstituted or substituted arylcarbonyl group, an unsubstituted or substituted heteroarylcarbonyl group, an unsubstituted or substituted alkoxycarbonyl group, an unsubstituted or substituted alkylsulfonyl group, or an unsubstituted or substituted arylsulfonyl group, A represents a hydroxyl group, a thiol group, an amino group, a nitro group, a halogen atom or an organic group, m represents any one of integers of 1 to 4, and k represents any one of integers of 0 to 3, wherein $k+m \leq 4$), with the proviso that 2-ethoxycarbonylamino-6-methylpyridine-N-oxide is excluded.

[2] A method for producing a substituted amino-6-methylpyridine-N-oxide derivative represented by formula (1-a) including oxidizing a substituted amino-6-methylpyridine derivative represented by formula (2) using a peroxide in the presence of a tungstophosphoric acid salt represented by formula (3):

[Chemical Formula 2]

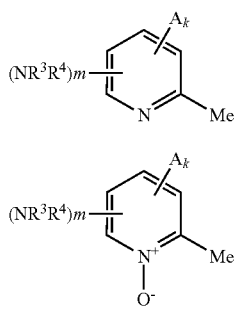

(2)

(1-a)

$Q_3[PW_4O_{24}]$ (3)

(in the formula,

A represents a hydroxyl group, a thiol group, an amino group, a nitro group, a halogen atom or an organic group, k represents any one of integers of 0 to 3, $R^3$ represents a hydrogen atom, an unsubstituted or substituted alkylcarbonyl group, an unsubstituted or substituted arylcarbonyl group, or an unsubstituted or substituted alkoxycarbonyl group, $R^4$ represents an unsubstituted or substituted alkylcarbonyl group, an unsubstituted or substituted arylcarbonyl group, an unsubstituted or substituted heteroarylcarbonyl group, an unsubstituted or substituted alkoxycarbonyl group, an unsubstituted or substituted alkylsulfonyl group, or an unsubstituted or substituted arylsulfonyl group, m represents any one of integers of 1 to 4, wherein $k+m \leq 4$, and Q represents a quaternary nitrogen cation).

[3] The method for producing a substituted amino-6-methylpyridine-N-oxide derivative according to the above aspect [2], wherein $R^3$ in formula (2) and in formula (1-a) is a hydrogen atom.

[4] The method for producing a substituted amino-6-methylpyridine-N-oxide derivative according to the above aspect [2], wherein the quaternary nitrogen cation represented by Q in formula (3) is a quaternary ammonium.

[5] The method for producing a substituted amino-6-methylpyridine-N-oxide derivative according to the above aspect [2], wherein the tungstophosphoric acid salt represented by formula (3) is obtained without an isolation operation after preparation.

[6] A method for producing a compound represented by formula (5) including reacting a compound represented by formula (4) with a halogenating agent:

[Chemical Formula 3]

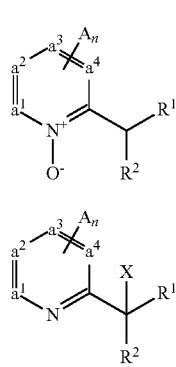

(4)

(5)

(in the formula, each of $a^1$ to $a^4$ independently represents a carbon atom, a nitrogen atom, an oxygen atom or a sulfur atom, each of $R^1$ and $R^2$ independently represents a hydrogen atom, or an unsubstituted or substituted alkyl group, and $R^1$ and $R^2$ may form a ring together, A represents a hydroxyl group, a thiol group, an amino group, a nitro group, a halogen atom or an organic group, n represents any one of integers of 0 to 4, and a plurality of A may be bonded to form a ring when n is 2 or more, and X represents a halogen atom).

[7] The method for producing a nitrogen-containing heterocyclic compound according to the above aspect [6], wherein all of $a^1$ to $a^4$ in formula (4) and formula (5) represent carbon atoms.

[8] The method for producing a nitrogen-containing heterocyclic compound according to the above aspect [6], wherein at least one of A in formula (4) and formula (5) represents a group represented by formula (6):

[Chemical Formula 4]

(6)

(in the formula (6), * indicates a binding site, $R^5$ represents a hydrogen atom, an unsubstituted or substituted alkylcarbonyl group, an unsubstituted or substituted arylcarbonyl group, an unsubstituted or substituted heteroarylcarbonyl group, an unsubstituted or substituted alkoxycarbonyl group, an unsubstituted or substituted alkylsulfonyl group, or an unsubstituted or substituted arylsulfonyl group, $R^6$ represents an unsubstituted or substituted alkylcarbonyl group, an unsubstituted or substituted arylcarbonyl group, an unsubstituted or substituted heteroarylcarbonyl group, an unsubstituted or substituted alkoxycarbonyl group, an unsubstituted or substituted alkylsulfonyl group, or an unsubstituted or substituted arylsulfonyl group, and $R^5$ and $R^6$ may be bonded to form a ring.)

[9] The method for producing a nitrogen-containing heterocyclic compound according to the above aspect [6], wherein the compound represented by formula (4) is a compound represented by formula (7), and the compound represented by formula (5) is a compound represented by formula (8):

[Chemical Formula 5]

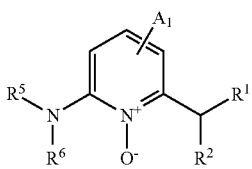
(7)

(in the formula (7), A, $R^1$ and $R^2$ are the same as defined above, l represents any one of integers of 0 to 3, $R^5$ represents a hydrogen atom, an unsubstituted or substituted alkylcarbonyl group, an unsubstituted or substituted arylcarbonyl group, an unsubstituted or substituted heteroarylcarbonyl group, an unsubstituted or substituted alkoxycarbonyl group, an unsubstituted or substituted alkylsulfonyl group, or an unsubstituted or substituted arylsulfonyl group, $R^6$ represents an unsubstituted or substituted alkylcarbonyl group, an unsubstituted or substituted arylcarbonyl group, an unsubstituted or substituted heteroarylcarbonyl group, an unsubstituted or substituted alkoxycarbonyl group, an unsubstituted or substituted alkylsulfonyl group, or an unsubstituted or substituted arylsulfonyl group, and $R^5$ and $R^6$ may be bonded to form a ring):

[Chemical Formula 6]

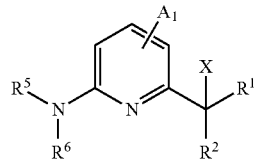
(8)

(in the formula (8), A, l, $R^1$, $R^2$, X, $R^5$ and $R^6$ are the same as defined above.)

[10] The method for producing a nitrogen-containing heterocyclic compound according to the above aspect [8], wherein $R^5$ represents an unsubstituted or substituted alkylcarbonyl group, an unsubstituted or substituted arylcarbonyl group, or an unsubstituted or substituted alkoxycarbonyl group.

[11] The method for producing a nitrogen-containing heterocyclic compound according to the above aspect [6], wherein the halogenating agent is at least one selected from the group consisting of thionyl chloride, thionyl bromide and sulfuryl chloride.

[12] The method for producing a nitrogen-containing heterocyclic compound according to the above aspect [6], wherein the reaction is carried out in the presence of a halogen ion source that is soluble in an organic solvent.

[13] The method for producing a nitrogen-containing heterocyclic compound according to the above aspect [6], wherein the halogenating agent is at least one selected from the group consisting of phosgene, diphosgene, triphosgene and phosphorus oxychloride.

[14] A method for producing a compound represented by formula (11) including a step of converting a compound represented by formula (9) into a compound represented by formula (10), and a step of reacting the compound represented by formula (10) with a halogenating agent to convert into the compound represented by formula (11):

[Chemical Formula 7]

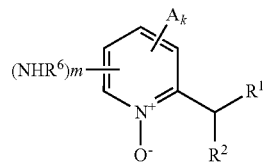
(9)

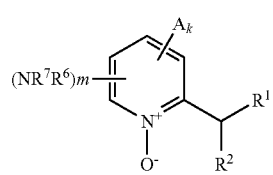
(10)

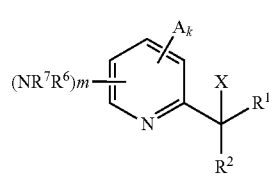
(11)

(in the formula, each of $R^1$ and $R^2$ independently represents a hydrogen atom, or an unsubstituted or substituted alkyl group, and $R^1$ and $R^2$ may form a ring together, R[6] represents an unsubstituted or substituted alkylcarbonyl group, an unsubstituted or substituted arylcarbonyl group, an unsubstituted or substituted heteroarylcarbonyl group, an unsubstituted or substituted alkoxycarbonyl group, an unsubstituted or substituted alkylsulfonyl group, or an unsubstituted or substituted arylsulfonyl group, R[7] represents an unsubstituted or substituted alkylcarbonyl group, an unsubstituted or substituted arylcarbonyl group, an unsubstituted or substituted heteroarylcarbonyl group, an unsubstituted or substituted alkoxycarbonyl group, an unsubstituted or substituted alkylsulfonyl group, or an unsubstituted or substituted arylsulfonyl group, A represents a hydroxyl group, a thiol group, an amino group, a nitro group, a halogen atom or an organic group, X represents a halogen atom, m represents any one of integers of 1 to 4, and k represents any one of integers of 0 to 3, wherein k+m≤4.)

[15] The method for producing a nitrogen-containing heterocyclic compound according to the above aspect [14], wherein a step of synthesizing the compound represented by formula (11) is carried out in the presence of a halogen ion source that is soluble in an organic solvent.

[16] A method for producing a compound represented by formula (13) including reacting a compound represented by formula (9) with a halogenating agent in the presence of a compound represented by formula (12):

[Chemical Formula 8]

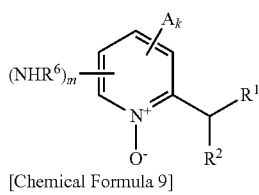

(9)

[Chemical Formula 9]

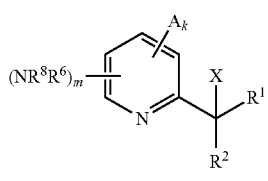

(13)

R[8]X[1]  (12)

(in the formula, each of R[1] and R[2] independently represents a hydrogen atom, or an unsubstituted or substituted alkyl group, and R[1] and R[2] may form a ring together, R[6] represents an unsubstituted or substituted alkylcarbonyl group, an unsubstituted or substituted arylcarbonyl group, an unsubstituted or substituted heteroarylcarbonyl group, an unsubstituted or substituted alkoxycarbonyl group, an unsubstituted or substituted alkylsulfonyl group, or an unsubstituted or substituted arylsulfonyl group, R[8] represents an unsubstituted or substituted alkylcarbonyl group, an unsubstituted or substituted arylcarbonyl group, or an unsubstituted or substituted alkoxycarbonyl group, A represents a hydroxyl group, a thiol group, an amino group, a nitro group, a halogen atom or an organic group, m represents any one of integers of 1 to 4, k represents any one of integers of 0 to 3, wherein k+m≤4, X represents a halogen atom, and X[1] represents a chlorine atom or a bromine atom).

[17] The method for producing a nitrogen-containing heterocyclic compound according to the above aspect [16], wherein the reaction is carried out in the presence of a halogen ion source that is soluble in an organic solvent.

[18] The production method according to the above aspect [12], [15] or [17], wherein the halogen ion source that is soluble in an organic solvent is a halogenated ammonium salt or a halogenated phosphonium salt.

[19] The production method according to the above aspect [12], [15] or [17], wherein the halogen ion source that is soluble in an organic solvent is a tertiary or quaternary alkyl ammonium halide salt having an alkyl group of $C_2$ or more, or an alkyl phosphonium halide salt having an alkyl group of $C_2$ or more.

[20] The production method according to any one of the above aspects [14] to [19], wherein the halogenating agent is at least one selected from the group consisting of thionyl chloride, thionyl bromide, phosphorus oxychloride, sulfuryl chloride, phosgene, diphosgene and triphosgene.

Advantageous Effects of Invention

According to the production method of the present invention, a substituted amino-pyridine-N-oxide derivative, a substituted amino-6-methylpyridine-N-oxide derivative, and a haloalkyl, nitrogen-containing heterocyclic derivative can be obtained with high selectivity and also in high yield. The nitrogen-containing heterocyclic compound obtained by the production method of the present invention is useful as an intermediate for the industrial production of agricultural chemicals or the like.

DESCRIPTION OF EMBODIMENTS

[1] Substituted amino-pyridine-N-oxide Derivative which is Useful as Synthetic Intermediate of Agricultural Chemicals or the Like A substituted amino-pyridine-N-oxide derivative which is useful as a synthetic intermediate of agricultural chemicals or the like according to the present invention is a compound represented by the formula (1).

In the formula (1), each of R[1] and R[2] independently represents a hydrogen atom, or an unsubstituted or substituted alkyl group. R[1] and R[2] may be bonded to form a ring.

It should be noted that in the present invention, the term "unsubstituted" means that the corresponding group is composed only of a core group.

On the other hand, in the present invention, the term "substituted" means that any one of hydrogen atoms constituting the core group has been substituted with a group having a different structure from that of the core group. Accordingly, the term "substituent" refers to another group which substitutes the core group. The number of substituents may be one or two or more. If two or more substituents are present, the substituents may be the same or may be different from each other.

Examples of the group which may serve as a "substituent" include a nitro group; a halogen atom such as a chlorine atom, a fluorine atom and a bromine atom; a hydroxy group; an alkoxy group such as a methoxy group, an ethoxy group, an i-propoxy group, an n-propoxy group, an n-butoxy group, an i-butoxy group, an s-butoxy group and a t-butoxy group; an aryloxy group such as a phenoxy group and a 1-naphthyloxy group; a haloalkoxy group such as a fluoromethoxy group, a difluoromethoxy group, a trifluoromethoxy group, a 2-chloroethoxy group, a 2,2,2-trichloroethoxy group, a 1,1,1,3,3,3- hexafluoro-2-propoxy group; an alkylthio group such as a methylthio group and an ethylthio group; an arylthio group such as a phenylthio group and a 1-naphthylthio group; an alkyl group such as a methyl group and an ethyl group; an aryl group such as a phenyl group and a naphthyl group; a heteroaryl group such as a pyrrolyl group, a thiazolyl group and a pyrimidinyl group; an alkylcarbonyl group; an arylcarbonyl group; a heteroarylcarbonyl group; an alkoxycarbonyl group; an alkylsulfonyl group; and an arylsulfonyl group.

Specific examples of the unsubstituted alkyl group for $R^1$ and $R^2$ include a methyl group, an ethyl group, an n-propyl group, an i-propyl group, an n-butyl group, an i-butyl group, an s-butyl group, a t-butyl group and an n-pentyl group, and $C_{1-6}$ alkyl groups are preferred.

Examples of the substituted alkyl group for $R^1$ and $R^2$ include a cyanoalkyl group such as a cyanomethyl group, a 1-cyanoethyl group and a 2-cyanoethyl group (cyano $C_{1-6}$ alkyl groups are preferred); a nitroalkyl group such as a nitromethyl group (nitro $C_{1-6}$ alkyl groups are preferred); a haloalkyl group such as a chloromethyl group, a fluoromethyl group, a difluoromethyl group, a trifluoromethyl group, a 2-fluoroethyl group and a 2,2,2-trifluoroethyl group (halo $C_{1-6}$ alkyl groups are preferred); an alkoxyalkyl group such as a methoxymethyl group, an ethoxymethyl group, a 1-methoxyethyl group and a 2-methoxyethyl group ($C_{1-6}$ alkoxy $C_{1-6}$ alkyl groups are preferred); an arylalkyl group such as a phenylmethyl group and a 1-naphthylethyl group ($C_{6-10}$ aryl $C_{1-6}$ alkyl groups are preferred); and a heteroarylalkyl group such as 2-pyridylmethyl group (5-6 membered heteroaryl $C_{1-6}$ alkyl groups are preferred).

Examples of the ring to be formed by the bonding of $R^1$ and $R^2$ include a cycloalkyl group such as a cyclopropyl group and a cyclobutyl group ($C_{3-8}$ cycloalkyl groups are preferred); a cycloalkenyl group such as a cyclohexenyl group ($C_{3-8}$ cycloalkenyl groups are preferred); and a saturated heterocyclic group such as a morpholino group (3 to 8-membered saturated heterocyclic groups are preferred).

In the formula (1), $R^3$ represents a hydrogen atom, an unsubstituted or substituted alkylcarbonyl group, an unsubstituted or substituted arylcarbonyl group, or an unsubstituted or substituted alkoxycarbonyl group.

Examples of the unsubstituted alkylcarbonyl group for $R^3$ include an acyl group and an ethylcarbonyl group, and $C_{1-6}$ alkylcarbonyl groups are preferred.

Examples of the substituted alkylcarbonyl group for $R^3$ include a cyano alkylcarbonyl group such as a cyano methylcarbonyl group (cyano $C_{1-6}$ alkyl carbonyl groups are preferred); a nitro alkyl carbonyl group such as a 1-nitro ethyl carbonyl group (nitro $C_{1-6}$ alkyl carbonyl groups are preferred); a haloalkylcarbonyl group such as a chloromethyl carbonyl group, a difluoromethyl carbonyl group and a 2,2,2-trifluoroethyl carbonyl group (halo $C_{1-6}$ alkyl carbonyl groups are preferred); an alkoxy alkyl carbonyl group such as a methoxy acyl group and a 2-methoxyethyl carbonyl group ($C_{1-6}$ alkoxy $C_{1-6}$ alkyl carbonyl groups are preferred); an aryl alkyl carbonyl group such as a phenyl methyl carbonyl group and a 1-naphthyl ethyl carbonyl group ($C_{6-10}$ aryl $C_{1-6}$ alkyl carbonyl groups are preferred); and a heteroaryl alkyl carbonyl group such as a 2-pyridyl methyl carbonyl group (5-6 membered heteroaryl $C_{1-6}$ alkyl carbonyl groups are preferred).

Examples of the unsubstituted arylcarbonyl group for $R^3$ include a benzoyl group and a 2-naphthyl carbonyl group, and $C_{6-10}$ arylcarbonyl groups are preferred.

Examples of the substituted arylcarbonyl group for $R^3$ include an arylcarbonyl group substituted with a nitro group, such as a 4-nitro phenyl carbonyl group ($C_{6-10}$ arylcarbonyl groups substituted with a nitro group are preferred); an arylcarbonyl group substituted with a cyano group such as a 2-cyanophenyl carbonyl group ($C_{6-10}$ arylcarbonyl groups substituted with a cyano group are preferred); an arylcarbonyl group substituted with an alkyl group such as a 2-methyl phenyl carbonyl group and a 3,5-dimethylphenyl carbonyl group ($C_{6-10}$ arylcarbonyl groups substituted with a $C_{1-6}$ alkyl group are preferred); and an arylcarbonyl group substituted with a halogen atom such as a 4-chlorophenyl carbonyl group and a 3,5-difluorophenyl carbonyl group ($C_{6-10}$ arylcarbonyl groups substituted with a halogen atom are preferred).

Examples of the unsubstituted alkoxycarbonyl group for $R^3$ include a methoxycarbonyl group and an ethoxycarbonyl group, and $C_{1-6}$ alkoxycarbonyl groups are preferred.

Examples of the substituted alkoxycarbonyl group for $R^3$ include a cyano alkoxycarbonyl group such as a cyano methoxycarbonyl group (cyano $C_{1-6}$ alkoxycarbonyl groups are preferred); a nitro alkoxycarbonyl group such as a 1-nitro ethoxycarbonyl group (nitro $C_{1-6}$ alkoxycarbonyl groups are preferred); a haloalkoxycarbonyl group such as a chloromethoxy carbonyl group, a difluoromethoxy carbonyl group and a 2,2,2-trifluoroethoxy carbonyl group (halo $C_{1-6}$ alkoxycarbonyl groups are preferred); an alkoxy alkoxycarbonyl group such as a methoxy carbonyl group and a 2-methoxyethoxy carbonyl group ($C_{1-6}$ alkoxy $C_{1-6}$ alkoxy carbonyl groups are preferred); an aryl alkoxycarbonyl group such as a phenyl methoxy carbonyl group and a 1-naphthyl ethoxy carbonyl group ($C_{6-10}$ aryl $C_{1-6}$ alkoxycarbonyl groups are preferred); and a heteroaryl alkoxy group such as a 2-pyridyl methoxy carbonyl group (5-6 membered heteroaryl $C_{1-6}$ alkoxycarbonyl groups are preferred).

In the formula (1), $R^4$ represents an unsubstituted or substituted alkylcarbonyl group, an unsubstituted or substituted arylcarbonyl group, an unsubstituted or substituted heteroarylcarbonyl group, an unsubstituted or substituted alkoxycarbonyl group, an unsubstituted or substituted alkylsulfonyl group, or an unsubstituted or substituted arylsulfonyl group.

Specific examples of the unsubstituted or substituted alkylcarbonyl group, the unsubstituted or substituted arylcarbonyl group, and the unsubstituted or substituted alkoxycarbonyl group for $R^4$ include the same as those described above as specific examples for $R^3$.

The heteroaryl carbonyl group for $R^4$ is one in which a monocyclic heteroaryl ring or fused heteroaryl ring containing at least one hetero atom selected from the group consisting of an oxygen atom, a nitrogen atom and a sulfur atom is bonded to a carbonyl group, and a 5- to 6-membered heteroaryl carbonyl group is preferred.

Examples of the unsubstituted heteroaryl carbonyl group for $R^4$ include a pyrrolyl carbonyl group, a furyl carbonyl group, a thienyl carbonyl group, an imidazolyl carbonyl group, a pyrazolyl carbonyl group, a thiazolyl carbonyl group, an isothiazolyl carbonyl group, an oxazolyl carbonyl group, an isooxazolyl carbonyl group, a triazolyl carbonyl group, a tetrazolyl carbonyl group, an oxadiazolyl carbonyl group, a 1,2,3-thiadiazolyl carbonyl group, a 1,2,4-thiadiazolyl carbonyl group, a 1,3,4-thiadiazolyl carbonyl group, a pyridyl carbonyl group, a pyrazinyl carboxy group, a pyrimidinyl carbonyl group, a pyridazinyl carboxyl group, a 1,2,4-triazinyl carbonyl group, a 1,3,5-triazinyl carbonyl group, an indolyl carbonyl group, a benzofuranylcarbonyl group, a benzothienylcarbonyl group, a benzimidazolylcarbonyl group, a benzopyrazolylcarbonyl group, a benzooxazolylcarbonyl group, a benzoisooxazolylcarbonyl group, a benzothiazolylcarbonyl group, a benzoisothiazolylcarbonyl group, an indazolylcarbonyl group, a purinylcarbonyl group, a quinolylcarbonyl group, an isoquinolylcarbonyl group, a phthalazinylcarbonyl group, a naphthyridinylcarbonyl group, a quinoxalinylcarbonyl group, a quinazolinylcarbonyl group, a cinnolinylcarbonyl group, a pteridinylcarbonyl group and a pyrido[3,2-b]pyridylcarbonyl group.

Examples of the substituted heteroaryl carbonyl group for $R^4$ include a heteroaryl carbonyl group substituted with a cyano group such as a 3-cyano-2-pyridylcarbonyl group; a heteroaryl carbonyl group substituted with a nitro group such as a 4-nitro-2-pyridylcarbonyl group; a heteroaryl carbonyl group substituted with a halogen atom such as a 5-fluoro-2-pyridylcarbonyl group; a heteroaryl carbonyl group substituted with an alkyl group such as a 6-methyl-2-pyridylcarbonyl group ($C_{1-6}$ alkyl 5-6 membered heteroaryl carbonyl groups are preferred); a heteroaryl carbonyl group substituted with an alkoxy group such as a 2-methoxy-3-pyridylcarbonyl group ($C_{1-6}$ alkoxy 5-6 membered heteroaryl carbonyl groups are preferred); a heteroaryl carbonyl group substituted with an aryl group such as a 4-phenyl-3-pyridylcarbonyl group ($C_{6-10}$ aryl 5-6 membered heteroaryl carbonyl groups are preferred); and a heteroaryl carbonyl group substituted with a heteroaryl group such as a 5-(2-pyridyl)-3-pyridylcarbonyl group (5-6 membered heteroaryl 5-6 membered heteroaryl carbonyl groups are preferred).

Examples of the unsubstituted alkylsulfonyl group for $R^4$ include a methylsulfonyl group and an ethylsulfonyl group, and $C_{1-6}$ alkylsulfonyl groups are preferred.

Examples of the substituted alkylsulfonyl group for $R^4$ include a cyano alkylsulfonyl group such as a cyano methylsulfonyl group (cyano $C_{1-6}$ alkylsulfonyl groups are preferred); a nitro alkylsulfonyl group such as a 1-nitro ethylsulfonyl group (nitro $C_{1-6}$ alkylsulfonyl groups are preferred); a haloalkylsulfonyl group such as a chloromethyl sulfonyl group, a difluoromethyl sulfonyl group and a 2,2,2-trifluoroethyl sulfonyl group (halo $C_{1-6}$ alkylsulfonyl groups are preferred); an alkoxy alkylsulfonyl group such as a methoxy methylsulfonyl group and a 2-methoxy ethylsulfonyl group ($C_{1-6}$ alkoxy $C_{1-6}$ alkylsulfonyl groups are preferred); an aryl alkylsulfonyl group such as a phenyl methylsulfonyl group and a 1-naphthyl ethyl sulfonyl group ($C_{6-10}$ aryl $C_{1-6}$ alkylsulfonyl groups are preferred); and a heteroaryl alkylsulfonyl group such as a 2-pyridyl methylsulfonyl group (5-6 membered heteroaryl $C_{1-6}$ alkylsulfonyl groups are preferred).

Examples of the unsubstituted arylsulfonyl group for $R^4$ include a phenylsulfonyl group and a 2-naphthylsulfonyl group, and $C_{6-10}$ arylsulfonyl groups are preferred.

Examples of the substituted arylsulfonyl group for $R^4$ include an arylsulfonyl group substituted with a cyano group such as a 2-cyano phenylsulfonyl group ($C_{6-10}$ arylsulfonyl groups substituted with a cyano group are preferred); an arylsulfonyl group substituted with a nitro group such as a 4-nitrophenylsulfonyl group ($C_{6-10}$ arylsulfonyl groups substituted with a nitro group are preferred); an arylsulfonyl group substituted with a halogen atom such as a 4-chlorophenylsulfonyl group and a 3,5-difluorophenylsulfonyl group ($C_{6-10}$ arylsulfonyl groups substituted with a halogen atom are preferred); an arylsulfonyl group substituted with an alkyl group such as a 2-methylphenylsulfonyl group and a 3,5-dimethyl phenylsulfonyl group ($C_{6-10}$ arylsulfonyl groups substituted with a $C_{1-6}$ alkyl group are preferred); and an arylsulfonyl group substituted with an alkoxy group such as a 4-methoxyphenylsulfonyl group ($C_{6-10}$ arylsulfonyl groups substituted with a $C_{1-6}$ alkoxy group are preferred).

In the formula (1), A represents a hydroxyl group, a thiol group, an amino group, a nitro group, a halogen atom or an organic group.

Examples of the halogen atom for A include a fluorine atom, a chlorine atom, a bromine atom and an iodine atom.

The organic group for A is a general description that represents all groups containing a carbon atom within a substituent, and examples thereof include a cyano group, an amino group having a substituent (amino groups substituted with a $C_{1-6}$ alkyl group or a $C_{6-10}$ aryl group are preferred); an unsubstituted or substituted alkyl group ($C_{1-6}$ alkyl groups substituted with a nitro group, a halogen atom, a $C_{1-6}$ alkoxy group or a $C_{6-10}$ aryl group are preferred), an unsubstituted or substituted alkenyl group ($C_{2-6}$ alkenyl groups substituted with a nitro group, a halogen atom, a $C_{1-6}$ alkoxy group or a $C_{6-10}$ aryl group are preferred), an unsubstituted or substituted alkynyl group ($C_{2-6}$ alkynyl groups substituted with a nitro group, a halogen atom, a $C_{1-6}$ alkoxy group or a $C_{6-10}$ aryl group are preferred), an unsubstituted or substituted aryl group ($C_{6-10}$ aryl groups substituted with a nitro group, a halogen atom, a $C_{1-6}$ alkyl group or a halo $C_{1-6}$ alkyl group are preferred), an unsubstituted or substituted heteroaryl group (5-6 membered heteroaryl groups substituted with a nitro group, a halogen atom, a $C_{1-6}$ alkyl group or a halo $C_{1-6}$ alkyl group are preferred), an unsubstituted or substituted alkoxy group ($C_{1-6}$ alkoxy groups substituted with a nitro group, a halogen atom, a $C_{1-6}$ alkoxy group or a $C_{6-10}$ aryl group are preferred), an unsubstituted or substituted alkenyloxy group ($C_{2-6}$ alkenyloxy groups substituted with a nitro group, a halogen atom, a $C_{1-6}$ alkoxy group or a $C_{6-10}$ aryl group are preferred), an unsubstituted or substituted alkynyloxy group ($C_{2-6}$ alkynyloxy groups substituted with a nitro group, a halogen atom, a $C_{1-6}$ alkoxy group or a $C_{6-10}$ aryl group are preferred), an unsubstituted or substituted aryloxy group ($C_{6-10}$ aryloxy groups substituted with a nitro group, a halogen atom, a $C_{1-6}$ alkyl group or a halo $C_{1-6}$ alkyl group are preferred), an unsubstituted or substituted heteroaryloxy group (5-6 membered heteroaryloxy groups substituted with a nitro group, a halogen atom, a $C_{1-6}$ alkyl group or a halo $C_{1-6}$ alkyl group are preferred), a formyl group, an unsubstituted or substituted alkylcarbonyl group ($C_{1-6}$ alkylcarbonyl groups substituted with a nitro group, a halogen atom, a $C_{1-6}$ alkoxy group or a $C_{6-10}$ aryl group are preferred), an unsubstituted or substituted alkenylcarbonyl group ($C_{2-6}$ alkenylcarbonyl groups substituted with a nitro group, a halogen atom, a $C_{1-6}$ alkoxy group or a $C_{6-10}$ aryl group are preferred), an unsubstituted or substituted alkynylcarbonyl group ($C_{2-6}$ alkynylcarbonyl groups substituted with a nitro group, a halogen atom, a $C_{1-6}$ alkoxy group or a $C_{6-10}$ aryl group are preferred), an unsubstituted or substituted arylcarbonyl group ($C_{6-10}$ arylcarbonyl groups substituted with a nitro group, a halogen atom, a $C_{1-6}$ alkyl group or a halo $C_{1-6}$ alkyl group are preferred), an unsubstituted or substituted heteroarylcarbonyl group (5-6 membered heteroarylcarbonyl groups substituted with a nitro group, a halogen atom, a $C_{1-6}$ alkyl group or a halo $C_{1-6}$ alkyl group are preferred), an unsubstituted or substituted alkylthio group ($C_{1-6}$ alkylthio groups substituted with a nitro group, a halogen atom, a $C_{1-6}$ alkoxy group or a $C_{6-10}$ aryl group are preferred), an unsubstituted or substituted alkenylthio group ($C_{2-6}$ alkenylthio groups substituted with a nitro group, a halogen atom, a $C_{1-6}$ alkoxy group or a $C_{6-10}$ aryl group are preferred), an unsubstituted or substituted alkynylthio group ($C_{2-6}$ alkynylthio groups substituted with a nitro group, a halogen atom, a $C_{1-6}$ alkoxy group or a $C_{6-10}$ aryl group are preferred), an unsubstituted or substituted arylthio group ($C_{6-10}$ arylthio groups substituted with a nitro group, a halogen atom, a $C_{1-6}$ alkyl group or a halo $C_{1-6}$ alkyl group are preferred), an unsubstituted or substituted heteroarylthio group (5-6 membered heteroarylthio groups substituted with a nitro group, a halogen atom, a $C_{1-6}$ alkyl group or a halo $C_{1-6}$ alkyl group are preferred), an unsubstituted or substituted alkylsulfinyl group ($C_{1-6}$ alkylsulfinyl groups substituted with a nitro group, a halogen atom, a $C_{1-6}$ alkoxy group or a $C_{6-10}$ aryl group are preferred), an unsubstituted or substituted alkenylsulfinyl group ($C_{2-6}$ alkenylsulfinyl groups substituted with a nitro group, a halogen atom, a $C_{1-6}$ alkoxy group or a $C_{6-10}$ aryl group are preferred), an unsubstituted or substituted alkynylsulfinyl group ($C_{2-6}$ alkynylsulfinyl groups substituted with a nitro group, a halogen atom, a $C_{1-6}$ alkoxy group or a $C_{6-10}$ aryl group are preferred), an unsubstituted or substituted arylsulfinyl group ($C_{6-10}$ arylsulfinyl groups substituted with a nitro group, a halogen atom, a $C_{1-6}$ alkyl group or a halo $C_{1-6}$ alkyl group are preferred), an unsubstituted or substituted heteroarylsulfinyl group (5-6 membered heteroarylsulfinyl groups substituted with a nitro group, a halogen atom, a $C_{1-6}$ alkyl group or a halo $C_{1-6}$ alkyl group are preferred), an unsubstituted or substituted alkylsulfonyl group ($C_{1-6}$ alkylsulfonyl groups substituted with a nitro group, a halogen atom, a $C_{1-6}$ alkoxy group or a $C_{6-10}$ aryl group are preferred), an unsubstituted or substituted alkenylsulfonyl group ($C_{2-6}$ alkenylsulfonyl groups substituted with a nitro group, a halogen atom, a $C_{1-6}$ alkoxy group or a $C_{6-10}$ aryl group are preferred), an unsubstituted or substituted alkynylsulfonyl group ($C_{2-6}$ alkynylsulfonyl groups substituted with a nitro group, a halogen atom, a $C_{1-6}$ alkoxy group or a $C_{6-10}$ aryl group are preferred), an unsubstituted or substituted arylsulfonyl group ($C_{6-10}$ arylsulfonyl groups substituted with a nitro group, a halogen atom, a $C_{1-6}$ alkyl group or a halo $C_{1-6}$ alkyl group are preferred), and an unsubstituted or substituted heteroarylsulfonyl group (5-6 membered heteroarylsulfonyl groups substituted with a nitro group, a halogen atom, a $C_{1-6}$ alkyl group or a halo $C_{1-6}$ alkyl group are preferred).

In the formula (1), m represents any one of integers of 1 to 4, and is preferably 1.

In the formula (1), k represents any one of integers of 0 to 3.

In addition, k+m≤4, with the proviso that 2-ethoxycarbonylamino-6-methylpyridine-N-oxide is excluded in the formula (1).

[2] Method for Producing Substituted amino-6-methylpyridine-N-oxide Derivative

The production method of the present invention includes oxidation of a substituted amino-6-methylpyridine derivative represented by formula (2) using a peroxide in the presence of a tungstophosphoric acid salt represented by formula (3). By the production method of the present invention, it is possible to obtain a substituted amino-6-methylpyridine-N-oxide derivative represented by formula (1-a).

The substituted amino-6-methylpyridine derivative used in the production method of the present invention is a compound represented by formula (2).

Specific examples of A, $R^3$ and $R^4$ in formula (2) or formula (1-a) include the same as those described above as specific examples in the aforementioned formula (1). m and k in formula (2) or formula (1-a) are the same as defined above as m and k in the aforementioned formula (1).

Among these, $R^3$ is preferably an unsubstituted or substituted alkoxycarbonyl group, more preferably an unsubstituted or substituted $C_{1-6}$ alkoxycarbonyl group, and still more preferably a t-butoxy group.

Among these, $R^4$ is preferably a hydrogen atom, or an unsubstituted or substituted arylcarbonyl group, more preferably a hydrogen atom or a benzoyl group, and still more preferably a hydrogen atom.

As a substitution position for $NR^3R^4$, the 2nd position of pyridine is preferred.

The substituted amino-6-methylpyridine derivative represented by the formula (2) can be obtained, for example, by reacting an acid chloride or acid anhydride with commercially available 2-amino-6-methylpyridine in the presence of a base such as pyridine or triethylamine More specifically, it is possible to obtain 2-[(t-butoxycarbonyl)amino]-6-methyl pyridine by using di-t-butyl dicarbonate in the reaction as the acid anhydride.

The tungstophosphoric acid salt used in the production method of the present invention is a compound represented by formula (3).

$[PW_4O_{24}]$ in formula (3) is a peroxotungsten heteropolyanion. The anion may also be represented by the formula $\{PO_4[W(O)(O_2)_2]_4\}$.

Q in the formula (3) represents a quaternary nitrogen cation.

As a quaternary nitrogen cation, there are quaternary ammonium, iminium, diazonium, cations of non-cyclic nitrogen skeletons, cations of nitrogen-containing cyclic skeletons, and the like.

Examples of the quaternary ammonium include tetramethylammonium, tetraethylammonium, tetra-(n-butyl)ammonium, tetraphenylammonium, tetrabenzylammonium, N,N,N-trimethylbenzylammonium, N,N,N-tri(n-butyl)benzylammonium, hexadecyltrimethylammonium, dihexadecyl dimethylammonium, trioctadecylmethylammonium, diocta decyldimethylammonium, trioctylmethylammonium, N,N,N-trimethylanilinium and N,N,N,N',N',N'-hexamethylethane-1,2-diaminium.

Examples of the iminium include benzylidene-t-butylmethylammonium and dibenzhydrylidene ammonium.

Examples of the diazonium include benzene diazonium, naphthalene-2-diazonium and benzene-1,4-bis(diazonium).

Examples of the cations of non-cyclic nitrogen skeletons include 1,1-dimethyl-1-phenyldiazan-1-ium, hexamethyldiazan-1,2-dium, 2,2-dimethyltriazan-2-ium, 1,2-dimethyltriazan-1-ium, 1,1,1,3-tetramethyltriaza-2-en-1-ium and 1H-4$\lambda^5$-pyrido[1,2,3-de]quinoxalin-4-ylium.

Examples of the cations of nitrogen-containing cyclic skeletons include 2,2-diethyl-2,5-diazabicyclo[4.2.2]decan-2-ium, 1,3-dimethylpyridin-1-ium, 3,7-dibromo-5-methylphenazin-5-ium, 1,3-dimethyl-1H-benzimidazol-3-ium, 1,1,4,4-tetramethylpiperazin-1,4-dium and cetyl pyridinium.

Among these, from the viewpoints of selectivity and reactivity, Q is preferably a quaternary ammonium, more preferably tetra-(n-butyl) ammonium or benzyltri(n-butyl)ammonium, and particularly preferably tetra-(n-butyl) ammonium.

The tungstophosphoric acid salt represented by the formula (3) can be obtained by the method described in Patent Document 4 or the like.

For example, by dissolving sodium tungstate (VI) in distilled water, adding an aqueous solution of phosphoric acid to the obtained solution, and then adding concentrated sulfuric acid to adjust the pH to an acidic range, followed by addition of hydrogen peroxide, stirring at room temperature, and then, adding a halogenated quaternary ammonium such as tetra-(n-butyl)ammonium chloride, it is possible to obtain the tungstophosphoric acid salt represented by the formula (3) such as tri[tetra-(n-butyl)ammonium]tetra(diperoxotungsto)phosphoric acid salt.

The tungstophosphoric acid salt represented by the formula (3) which is used in the production method of the present invention can be isolated and purified after preparation to be subjected to an oxidation reaction, although it can also be subjected to an oxidation reaction continuously without carrying out an isolation operation. From the viewpoint of ease of operation, the prepared tungstophosphoric acid salt which is represented by the formula (3) is preferably subjected to an oxidation reaction continuously without carrying out an isolation operation. It should be noted that the isolation operation includes filtration, washing, and the like.

The used amount of tungstophosphoric acid salt represented by the formula (3) is not particularly limited, although it is preferably 0.001 mol % to 1,000 mol %, more preferably 0.01 mol % to 100 mol %, and particularly preferably 0.1 mol % to 10 mol %, relative to the substituted amino-6-methylpyridine derivative represented by the formula (2).

The peroxide used in the oxidation reaction in the production method of the present invention is not particularly limited. Examples thereof include organic peroxides such as dicumyl peroxide, 1,1-di-t-butylperoxy-3,3,5-trimethylcyclohexane, 1,1-di-t-butyl peroxycyclohexane, 2,2-di-t-butyl peroxybutane, n-butyl 4,4-t-butyl peroxyvalerate, 2,2-bis(4,4-di-t-butylperoxycyclohexane)propane, 2,2,4-trimethylpentyl peroxyneodecanoate, α-cumyl peroxyneodecanoate, t-butyl peroxyneohexanoate, t-butyl peroxyacetate, t-butyl peroxylaurate, t-butyl peroxybenzoate, t-butyl peroxyisophthalate, peracetic acid and performic acid; and inorganic peroxides such as hydrogen peroxide and sodium peroxide.

Of these, hydrogen peroxide is preferred from the viewpoints of safety, economy and selectivity.

The used amount of peroxide is not particularly limited, although it is preferably 100 mol % to 2,000 mol %, more preferably 100 mol % to 1,000 mol %, and particularly preferably 100 mol % to 200 mol %, relative to the substituted amino-6-methylpyridine derivative represented by the formula (2).

In addition, an aqueous hydrogen peroxide solution may be used as the peroxide. The concentration of the aqueous hydrogen peroxide solution is not particularly limited, although it is preferably 0.1 to 70% by weight, more preferably 5 to 40% by weight, and particularly preferably 30 to 35% by weight.

In the production method of the present invention, the reaction may be carried out in the presence of an organic solvent. The organic solvent is not particularly limited as long as it is an organic solvent capable of dissolving the substituted amino-6-methylpyridine derivative represented by the formula (2) without being oxidized. Examples thereof include acetonitrile, benzene, acetone, methylene chloride, chloroform and dioxane. For example, when using hydrogen peroxide as the peroxide, as a solvent, methylene chloride or chloroform is preferred, and chloroform is particularly preferred.

The temperature from the start of the oxidation reaction until the end of the oxidation reaction is not particularly limited, although the temperature is preferably from −78° C. to 200° C., more preferably from −20° C. to 120° C., and particularly preferably from 10° C. to 100° C. When the temperature is too high, side reactions tend to proceed. When the temperature is too low, the reactions tend to proceed poorly. The time for the oxidation reaction may be appropriately selected depending on the scale of the reaction. The progress of the reaction may be observed, for example, by general analysis, such as gas chromatography, high-performance liquid chromatography, thin layer chromatography, NMR or IR.

By the oxidation reaction as described above, it is possible to obtain a substituted amino-6-methylpyridine-N-oxide derivative represented by formula (1-a). After completion of the oxidation reaction, the substituted amino-6-methylpyridine-N-oxide derivative represented by formula (1-a) which has been generated may be isolated. The isolation method may be appropriately selected in accordance with the type of peroxide used in the oxidation reaction or the nature of the target product. For example, when hydrogen peroxide is used as the peroxide, after the completion of the oxidation reaction or after decomposing the remaining hydrogen peroxide with a reducing agent such as sodium sulfite, water and an organic solvent, if necessary, are added to the reaction solution, followed by performing an extraction and liquid separation operation, and then concentrating the separated organic layer to isolate a desired product.

In addition, an aqueous layer obtained by the liquid separation operation contains a tungstophosphoric acid salt represented by formula (3), and therefore the aqueous layer may be reused as it is or after conducting a concentration treatment or the like as needed for the oxidation reaction in the production method of the present invention.

The production method of the present invention is economical because the removal of tungstophosphoric acid salt represented by the formula (3) after the reaction is easy, and the reuse thereof is also possible.

In addition, the substituted amino-6-methylpyridine-N-oxide derivative represented by formula (1-a) which is obtained by the production method of the present invention is useful as an intermediate in the manufacture of agricultural chemicals or the like.

[3] Method for Producing Haloalkyl-Nitrogen-Containing Heterocyclic Derivative

[3-1] First Embodiment

The method for producing a haloalkyl nitrogen-containing heterocyclic compound according to the present invention includes a step of reacting a compound represented by formula (4) with a halogenating agent to synthesize a compound represented by formula (5).

The raw material used in the production method of the present invention is a compound represented by formula (4).

In the formula (4), each of $a^1$, $a^2$, $a^3$ and $a^4$ independently represents a carbon atom, a nitrogen atom, an oxygen atom or a sulfur atom. Of the possibilities, it is preferable that all of $a^1$, $a^2$, $a^3$ and $a^4$ represent a carbon atom.

Specific examples of $R^1$, $R^2$ and A in formula (4) include the same as those described above as specific examples in the aforementioned formula (1).

n indicates the number of substitutents of A, and is any one of integers of 0 to 4. When n is 2 or more, each A may be the same or may be different from each other.

In addition, more than one A may be bonded with each other to form a ring, such as a quinoline ring, an isoquinoline ring, a 2,6-naphthyridine ring, a 1,8-naphthyridine ring, a phthalazine ring, a quinoxaline ring, a quinazoline ring, a pteridine ring, or a purine ring.

In the present invention, at least one of A is preferably a group represented by formula (6).

In the formula (6), * indicates a binding site.

In the formula (6), $R^5$ represents a hydrogen atom, an unsubstituted or substituted alkylcarbonyl group, an unsubstituted or substituted arylcarbonyl group, an unsubstituted or substituted heteroarylcarbonyl group, an unsubstituted or substituted alkoxycarbonyl group, an unsubstituted or substituted alkylsulfonyl group, or an unsubstituted or substituted arylsulfonyl group, and specific examples thereof include the same as those described above as specific examples for $R^4$ in the aforementioned formula (1). Of these, an unsubstituted or substituted alkylcarbonyl group (more preferably, an unsubstituted or substituted $C_{1-6}$ alkylcarbonyl group), an unsubstituted or substituted arylcarbonyl group (more preferably, an unsubstituted or substituted $C_{6-10}$ arylcarbonyl group), or an unsubstituted or substituted alkoxycarbonyl group (more preferably, an unsubstituted or substituted $C_{1-6}$ alkoxycarbonyl group) is preferable.

In the formula (6), $R^6$ represents an unsubstituted or substituted alkylcarbonyl group, an unsubstituted or substituted arylcarbonyl group, an unsubstituted or substituted heteroarylcarbonyl group, an unsubstituted or substituted alkoxycarbonyl group, an unsubstituted or substituted alkylsulfonyl group, or an unsubstituted or substituted arylsulfonyl group, and specific examples thereof include the same as those described above as specific examples for $R^4$ in the aforementioned formula (1).

$R^5$ and $R^6$ may be bonded to form a ring.

In the production method of the present invention, among the compounds represented by formula (4) that are raw materials, a compound represented by formula (7) is preferably used.

In the formula (7), A, $R^1$, $R^2$, $R^5$ and $R^6$ are the same as A, $R^1$, $R^2$, $R^5$ and $R^6$ defined above in formula (4) and formula (6).

In the formula (7), l indicates the number of substituents of A, and is any one of integers from 0 to 3. When l is 2 or more, each A may be the same or may be different from each other, and may also be bonded with each other to form a ring.

The compounds represented by the formula (4) or formula (7) may be obtained by oxidizing the corresponding 2-picoline derivative using a known method, for example, an oxidation method using meta-chloroperbenzoic acid, an oxidation method using hydrogen peroxide in the presence of tungstic acid (refer to U.S. Pat. No. 3,047,579), or the like.

(Halogenating Agent)

The halogenating agent used in the present invention is not particularly limited as long as it is an agent used for halogenation in a known synthesis reaction.

Examples of the halogenating agent include thionyl chloride, thionyl bromide, sulfuryl chloride, phosgene, diphosgene, triphosgene and phosphorus oxychloride.

Among these, thionyl chloride, thionyl bromide or sulfuryl chloride is capable of suppressing the generation of byproducts and increasing the selectivity and yield for the synthesis reaction of the compound represented by formula (4), even without the presence of a halogen ion source described later.

In addition, phosgene, diphosgene, triphosgene or phosphorus oxychloride allows the reaction to proceed under mild conditions and also increases the selectivity and yield for the synthesis reaction of the compound represented by formula (4). Phosgene, diphosgene, triphosgene or phosphorus oxychloride may be suitably used when $R^5$ in the formula (6) represents a hydrogen atom.

The amount of the halogenating agent used is not particularly limited, although it is preferably from 0.8 to 10 equivalent, and more preferably from 1.5 to 2.5 equivalents, relative to the compound represented by formula (4). However, for diphosgene and triphosgene, it is preferable to convert each of the equivalent values described above for phosgene for use.

(Halogen Ion Source)

The halogen ion source soluble in organic solvents which is used in the present invention is a salt containing a halogen anion which is soluble in organic solvents.

Examples of the halogen ion source include an ammonium halide salt, preferably a tertiary or quaternary alkyl ammonium halide salt, and more preferably a triethylamine hydrohalide salt or a di-1-propylethylamine hydrohalide salt.

In addition, examples of other halogen ion sources that are soluble in organic solvents include a phosphonium halide salt, preferably an alkyl phosphonium halide salt having an alkyl group of $C_2$ or more.

By making a halogen ion source which is soluble in an organic solvent to be present in the reaction system, it is possible to suppress the generation of byproducts, and to increase the selectivity and yield for the synthesis reaction of the compound represented by formula (4). The halogen ion source exhibits more significant effects when phosgene, diphosgene, triphosgene or phosphorus oxychloride is used as a halogenating agent.

The used amount of the halogen ion source which is soluble in organic solvents is not particularly limited, although it is preferably 0.8 times or more the molar amount of the halogen atom, and more preferably 1 to 6 times the molar amount of the halogen atom, relative to the compound represented by formula (4).

(Organic Solvent)

In the production method of the present invention, it is possible to use an organic solvent. Usable organic solvents are not particularly limited, although haloalkanes are preferred, and methylene chloride or chloroform is more preferred.

(Other Reaction Sub-Materials)

In the production method of the present invention, it is preferable that a deoxidizing agent be present, in addition to the halogen ion source. An amine soluble in organic solvents is desirable as the deoxidizing agent, and tertiary alkyl amines having an alkyl group of $C_2$ or more are more preferred, and triethylamine or di-i-propylethyl amine is particularly preferred.

The amount of the deoxidizing agent used is preferably at least an amount that may almost completely capture the hydrogen halide generated as a result of the reaction, and more specifically, at least one time the molar amount of hydrogen halide generated. The upper limit of the amount used is preferably six times the molar amount of hydrogen halide generated. In the present invention, the coexistence of a halogen ion source and a deoxidizing agent is preferred.

(Reaction Between Compound Represented by Formula (4) and Halogenating Agent)

The reaction between the compound represented by the formula (4) and the halogenating agent is not particularly limited in terms of the technique employed. For example, the reaction may be carried out by dissolving a halogen ion source and a deoxidizing agent that are used as necessary in an organic solvent, adding the compound represented by formula (4) to the solution, followed by the addition of a halogenating agent thereto. In the present invention, in order to achieve especially high yield, it is preferable to dissolve the halogen ion source and the deoxidizing agent that are used as necessary in an organic solvent, followed by adding the compound represented by formula (4) and the halogenating agent almost simultaneously to the solution. The addition of the halogenating agent may be carried out by dropwise addition of an organic solvent solution of the halogenating agent or by blowing in a gaseous halogenating agent. Moreover, addition of the compound represented by formula (4) may be carried out by the dropwise addition of the liquid.

The temperature from the start of the reaction until the end of the reaction is not particularly limited, although in view of enhancing the selectivity, the temperature is preferably not more than 40° C., and more preferably within the range from −40° C. to 20° C.

By the production method of the present invention, it is possible to obtain a compound represented by formula (5). A, $a^1$, $a^2$, $a^3$, $a^4$, $R^1$, $R^2$ and n in formula (5) are the same as defined above for A, $a^1$, $a^2$, $a_3$, $a^4$, $R^1$, $R^2$ and n in formula (4). X represents a halogen atom such as a fluorine atom, a chlorine atom, a bromine atom or an iodine atom. It should be noted that in the cases where the compound represented by formula (4) serving as a raw material is a compound represented by formula (7), it is possible to obtain a compound represented by formula (8). In the formula (8), A, 1, $R^1$, $R^2$, $R^5$ and $R^6$ are the same as defined above for A, 1, $R^1$, $R^2$, $R^5$ and $R^6$ in formula (7), and X represents a halogen atom.

[3-2] Second Embodiment

The method for producing a nitrogen-containing heterocyclic compound according to the present invention includes a step of converting a compound represented by formula (9) into a compound represented by formula (10), and a step of reacting the compound represented by the formula (10) with a halogenating agent to synthesize a compound represented by formula (11).

The raw material used in the production method of the present invention is a compound represented by formula (9). The compound corresponds to a compound represented by the formula (4) in which all of $a^1$, $a^2$, $a^3$ and $a^4$ represent carbon atoms and also at least one of A is a group represented by formula (6a). It should be noted that * indicates a binding site in the formula (6a).

[Chemical Formula 10]

(6a)

Specific examples of A, $R^1$ and $R^2$ in formula (9) include the same as those described above as specific examples in the aforementioned formulae (4) and (5). In addition, k and m in formula (9), formula (10) and formula (11) are the same as defined above for k and m in the formula (1).

In the formula (9) or formula (6a), $R^6$ represents an unsubstituted or substituted alkylcarbonyl group, an unsubstituted or substituted arylcarbonyl group, an unsubstituted or substituted heteroarylcarbonyl group, an unsubstituted or substituted alkoxycarbonyl group, an unsubstituted or substituted alkylsulfonyl group, or an unsubstituted or substituted arylsulfonyl group, and specific examples thereof include the same as those described above as specific examples for $R^3$ and $R^4$. Of these, an unsubstituted or substituted alkylcarbonyl group, an unsubstituted or substituted arylcarbonyl group, an unsubstituted or substituted heteroarylcarbonyl group, or an unsubstituted or substituted alkoxycarbonyl group is preferred, an unsubstituted or substituted alkoxycarbonyl group is more preferred, and an unsubstituted or substituted $C_{3-8}$ alkoxycarbonyl group is particularly preferred.

The compounds represented by formula (9) (except for 2-ethoxycarbonyl amino-6-methyl pyridine-N-oxide) are novel substances. The compound may be obtained by a method in which the corresponding 2-picoline derivative is oxidized with meta-chloroperbenzoic acid, a method in which the corresponding 2-picoline derivative is oxidized with hydrogen peroxide in the presence of tungstic acid (refer to U.S. Pat. No. 3,047,579), or the like.

(Step of Converting Compound Represented by Formula (9) into Compound Represented by Formula (10))

Examples of the method to convert a compound represented by formula (9) into a compound represented by formula (10) include a method in which a compound represented by $R^7X^1$ is reacted with the compound represented by formula (9). Here, $R^7$ is the same as $R^7$ in the formula (10) described later, and $X^1$ represents a chlorine atom or a bromine atom.

By going through the conversion step, it is possible to obtain a compound represented by formula (10).

A, k, $R^1$, $R^2$, $R^6$ and m in formula (10) are the same as defined above for A, k, $R^1$, $R^2$, $R^6$ and m in formula (9).

In the formula (10), $R^7$ represents an unsubstituted or substituted alkylcarbonyl group, an unsubstituted or substituted arylcarbonyl group, an unsubstituted or substituted heteroarylcarbonyl group, an unsubstituted or substituted alkoxycarbonyl group, an unsubstituted or substituted alkylsulfonyl group, or an unsubstituted or substituted arylsulfonyl group, and specific examples thereof include the same as those described above as specific examples for $R^3$ and $R^4$. When m is 2 or more, each $R^7$ may be the same or may be different from each other.

(Reaction Between Compound Represented by Formula (10) and Halogenating Agent)

For the reaction between a compound represented by formula (10) and a halogenating agent, the same technique as that used in the reaction between a compound represented by formula (4) and a halogenating agent in the first embodiment may be employed. In addition, examples of the halogenating agents, halogen ion sources, organic solvents and other reaction auxiliary materials that may be used in the second embodiment include the same as those that may be used in the first embodiment.

By the production method according to the second embodiment of the present invention, it is possible to obtain a compound represented by formula (11).

In the formula (11), A, k, $R^1$, $R^2$, $R^6$, $R^7$ and m are the same as defined above for A, k, $R^1$, $R^2$, $R^6$, $R^7$ and m in the aforementioned formula (9) and formula (10).

In the formula (11), X represents a halogen atom such as a fluorine atom, a chlorine atom, a bromine atom or an iodine atom.

[3-3] Third Embodiment

The method for producing a nitrogen-containing heterocyclic compound according to the present invention includes a step of reacting the compound represented by formula (9) with a halogenating agent in the presence of a compound represented by formula (12) to synthesize a compound represented by formula (13).

For the method for reacting the compound represented by formula (9) with a halogenating agent in the presence of a compound represented by formula (12), the same technique as that used in the method to react the compound represented by formula (4) with a halogenating agent in the first embodiment may be employed, with the exception that the compound represented by formula (12) is present in the reaction system. In addition, examples of the halogenating agents, halogen ion sources, organic solvents and other reaction auxiliary materials that may be used in the third embodiment include the same as those that may be used in the first embodiment.

By the production method according to the third embodiment of the present invention, it is possible to obtain a compound represented by formula (13).

In the formula (12), $R^8$ represents an unsubstituted or substituted alkylcarbonyl group, an unsubstituted or substituted arylcarbonyl group, or an unsubstituted or substituted alkoxycarbonyl group, and specific examples thereof include the same as those described above as specific examples for $R^3$. In addition, $X^1$ in the formula (12) represents a chlorine atom or a bromine atom.

In the formula (13), specific examples of A, $R^1$, $R^2$, $R^6$ and $R^8$ include the same as those described above as specific examples for A, $R^1$, $R^2$, $R^6$ and $R^8$ in the aforementioned formula (9) and formula (12). In the formula (13), k and m are the same as defined above for k and m in the aforementioned formula (9) and formula (12). In addition, X in the formula

(13) represents a halogen atom such as a fluorine atom, a chlorine atom, a bromine atom or an iodine atom.

The compounds represented by the formula (5), (8), (11) or (13) that are obtained by the production method of the present invention are useful as intermediates for the synthesis of agricultural chemicals, pharmaceutical products, or the like.

EXAMPLES

The present invention will be described in more detail below using a series of examples and comparative examples. However, the technical scope of the present invention is in no way limited by these examples.

Example A1

1.65 g (5 mmol) of sodium tungstate(VI)dihydrate ($Na_2WO_4.2H_2O$) was dissolved in 20 ml of distilled water. 6 ml of 10% phosphoric acid ($H_3PO_4$) was added to the obtained solution, and concentrated sulfuric acid was then added thereto to adjust the pH to 2.0.

8 ml of a 25% aqueous hydrogen peroxide solution was added to the solution, and the resulting mixture was stirred at room temperature for 20 minutes. An aqueous solution of tetra(n-butyl) ammonium chloride (4 mol) was slowly added dropwise to the reaction mixture which had been stirred vigorously. After the completion of the dropwise addition, the resulting mixture was stirred at room temperature for 50 minutes.

The obtained reaction solution was filtered, and the residue was washed with water. The obtained residue was dissolved in chloroform and was then dehydrated and dried with anhydrous sodium sulfate, and the obtained solution was filtered. Then, the solvent was removed from the filtrate by distillation, thereby yielding colorless crystals ($[(n-C_4H_9)_4N]_3[PW_4O_{24}]$).

0.567 g of a 30% aqueous hydrogen peroxide solution was charged into a reaction vessel. 0.093 g of the tungstophosphoric acid salt obtained above was added thereto.

Subsequently, 1.25 ml of a methylene chloride solution of 2-[(t-butoxycarbonyl)amino]-6-methyl pyridine having a concentration of 2 mol/L was added thereto, and the resulting mixture was stirred at room temperature for 20 minutes. Then, the mixture was stirred for 1 hour while refluxing.

2 ml of water and 3 ml of methylene chloride were added to the reaction solution, followed by extraction and liquid separation. The resulting aqueous layer was extracted twice with 3 ml of methylene chloride, and all of the obtained organic layers were brought together. The resulting organic layer was analyzed by HPLC. As a result, it was shown that 2-[(t-butoxycarbonyl)amino]-6-methyl pyridine-N-oxide was obtained with a yield of 97.6%.

The measurement results of $^1H$-NMR spectrum of the obtained 2-[(t-butoxycarbonyl)amino]-6-methyl pyridine-N-oxide were as follows.

$^1H$-NMR ($CDCl_3$, δ ppm): 1.53 (9H, s), 2.55 (3H, s), 6.87 (1H, d, J=7.6 Hz), 7.19 (1H, t, J=8.2 Hz), 8.01 (1H, d, J=8.8 Hz), 9.43 (1H, brs).

Example A2

0.2 g of a 10% aqueous phosphoric acid solution ($H_3PO_4$) was added to a reaction vessel charged with 0.041 g of sodium tungstate(VI)dihydrate ($Na_2WO_4.2H_2O$), and 0.567 g of a 30% aqueous hydrogen peroxide solution was then added thereto.

Subsequently, 0.031 g of benzyltri(n-butyl)ammonium chloride was added thereto, and the resulting mixture was stirred at room temperature for 10 minutes. White crystals precipitated in the reaction solution.

Subsequently, 1.25 ml of a methylene chloride solution of 2-[(t-butoxycarbonyl)amino]-6-methyl pyridine having a concentration of 2 mol/l was added thereto, and the resulting mixture was stirred at room temperature for 5 minutes. Then, the mixture was stirred for 2 hours while refluxing.

5 ml of water was added to the obtained reaction solution for extraction and liquid separation, and the resulting aqueous layer was extracted twice with 3 ml of methylene chloride. All of the obtained organic layers were brought together. The resulting organic layer was analyzed by HPLC. As a result, it was shown that 2-[(t-butoxycarbonyl)amino]-6-methyl pyridine-N-oxide was obtained with a yield of 97.1%.

Example A3

1.63 g of a 10% aqueous phosphoric acid solution ($H_3PO_4$) was added to a reaction vessel charged with 0.274 g of sodium tungstate(VI)dihydrate ($Na_2WO_4.2H_2O$), and 2.45 g of a 30% aqueous hydrogen peroxide solution was then added thereto.

Subsequently, 0.207 g of benzyltri(n-butyl)ammonium chloride was added thereto, and the resulting mixture was stirred at room temperature for 10 minutes. White crystals precipitated in the reaction solution.

Subsequently, 8.3 ml of a chloroform solution of 2-[(t-butoxycarbonyl)amino]-6-methyl pyridine having a concentration of 2 mol/l was added thereto, and the resulting mixture was stirred at room temperature for 5 minutes. Then, the mixture was stirred for 2 hours while refluxing.

10 ml of water was added to the obtained reaction solution for extraction and liquid separation, and the resulting aqueous layer was extracted twice with 5 ml of chloroform. All of the obtained organic layers were brought together. The resulting organic layer was analyzed by HPLC. As a result, it was shown that 2-[(t-butoxycarbonyl)amino]-6-methyl pyridine-N-oxide was obtained with a yield of almost 100%.

From the results shown above, it is clear that a substituted amino-6-methylpyridine-N-oxide derivative can be obtained with high selectivity by oxidizing a substituted amino-6-methylpyridine derivative using a peroxide, such as hydrogen peroxide, in the presence of a tungstophosphoric acid salt, such as $[(n-C_4H_9)_4N]_3[PW_4O_{24}]$ or $[(C_6H_5CH_2)(n-C_4H_9)_3N]_3[PW_4O_{24}]$. In addition, from a comparison between Example A1 and Example A2, it is apparent that the selectivity of the oxidation reaction of a substituted amino-6-methylpyridine derivative does not decline, even when a tungstophosphoric acid salt is used as it is in the oxidation reaction without isolation after the preparation thereof. From a comparison between Example A2 and Example A3, it is evident that a target product can be obtained with a high yield with a smaller amount of catalyst and oxidizing agent when chloroform is used as a reaction solvent.

Example B1

7 ml of a methylene chloride solution containing 0.54 g (2.4 mmol) of 2-t-butoxycarbonyl amino-6-methyl pyridine-N-oxide was cooled to −17° C. 0.63 g (5.3 mmol) of thionyl chloride was added thereto, and 3 ml of a methylene chloride solution containing 1.02 g (8.6 mmol) of triethylamine was then added dropwise thereto. The reaction was allowed to proceed for 3 hours at −15° C. Then, 20 ml of water was added thereto at −10° C. Then, the pH was adjusted to 11 with caustic soda. 2-t-butoxycarbonyl amino-6-chloromethyl pyridine which was the target product was obtained with a yield of 60% in the organic layer obtained by liquid separation.

Example B2

A solution A was prepared by dissolving 1.35 g (6.0 mmol) of 2-t-butoxycarbonyl amino-6-methyl pyridine-N-oxide in 18 ml of methylene chloride and was cooled to −15° C.

A solution B was prepared by dissolving 1.57 g (13.2 mmol) of thionyl chloride in 18 ml of methylene chloride.

A solution C was prepared by dissolving 2.43 g (24.0 mmol) of triethylamine in 18 ml of methylene chloride.

The solution B was added dropwise to the solution A. When 5 minutes had elapsed from the start of the dropwise addition, the dropwise addition of solution C was started. The solution B was added dropwise over 70 minutes and the solution C was added dropwise over 105 minutes, so that each of the solutions was added entirely. When one hour had elapsed after the completion of the dropwise addition, 100 ml of water was added thereto. Then, the pH was adjusted to 3.7 by adding saturated sodium bicarbonate water thereto. 2-t-butoxycarbonyl amino-6-chloromethyl pyridine which was the target product was obtained with a yield of 62% in the organic layer obtained by liquid separation.

Example B3

0.3 g (3.0 mmol) of triethylamine and 2.48 g (18.0 mmol) of triethylamine hydrochloride were dissolved in 18 ml of methylene chloride. The solution was cooled to −14° C., and 18 ml of a methylene chloride solution containing 1.34 g (6.0 mmol) of 2-t-butoxycarbonyl amino-6-methyl pyridine-N-oxide and 2.13 g (21.1 mmol) of triethylamine and 18 ml of a methylene chloride solution containing 1.57 g (13.2 mmol) of thionyl chloride were added dropwise at the same time. The reaction was allowed to proceed for 2 hours at −15° C. Then, 15 ml of water was added thereto. Then, the pH was adjusted to 13 with caustic soda. After liquid separation, the organic layer was washed with dilute hydrochloric acid. 2-t-butoxycarbonyl amino-6-chloromethyl pyridine which was the target product was obtained with a yield of 55% in the resulting organic layer.

Example B4

0.31 g (3.1 mmol) of triethylamine and 2.57 g (18.7 mmol) of triethylamine hydrochloride were dissolved in 18 ml of chloroform. The solution was cooled to −14° C., and 18 ml of a chloroform solution containing 1.34 g (6.0 mmol) of 2-t-butoxycarbonyl amino-6-methyl pyridine-N-oxide and 2.20 g (21.8 mmol) of triethylamine and 18 ml of a methylene chloride solution containing 1.63 g (13.7 mmol) of thionyl chloride were added dropwise at the same time over 105 minutes. The reaction was allowed to proceed for 2 hours at −15° C. Then, 30 ml of water was added thereto. Then, the pH was adjusted to 5 with saturated sodium bicarbonate water. 2-t-butoxycarbonyl amino-6-chloromethyl pyridine which was the target product was obtained with a yield of 77% in the organic layer obtained by liquid separation.

Example B5

0.224 g (1.0 mmol) of 2-t-butoxycarbonyl amino-6-chloromethyl pyridine-N-oxide was dissolved in 2 ml of chloroform. While ice-cooling the resultant with stirring, 0.139 ml (1.0 mmol) of triethylamine, 0.174 ml (1.5 mmol) of benzoyl chloride, 0.088 ml (1.2 mmol) of thionyl chloride and 0.14 g (1.0 mmol) of triethylamine hydrochloride were sequentially added thereto. After completion of the addition, 0.418 ml (3.0 mmol) of triethylamine which was dissolved in 2 ml of chloroform was added dropwise over 15 minutes. After the completion of the dropwise addition, the resulting mixture was stirred under ice cooling for 5 minutes, and then at room temperature for 30 minutes. Then, the resultant was quantitatively analyzed by HPLC. 2-benzoyl-t-butoxycarbonyl amino-6-chloromethyl pyridine which was the target product was obtained with a yield of 72%.

Example B6

1 ml of a chloroform solution containing 0.22 g (1.0 mmol) of 2-t-butoxycarbonyl amino-6-methyl pyridine-N-oxide was added dropwise to 5 mL of a chloroform solution containing 2.0 mmol of para-nitrobenzoyl chloride over 10 minutes at room temperature. After 20 minutes had elapsed therefrom, the reaction mixture was cooled to −15° C., and 0.30 g (3.0 mmol) of triethylamine was added dropwise thereto over 5 minutes. After 5 minutes had elapsed therefrom, 1 ml of a chloroform solution containing 0.20 g (0.67 mmol) of triphosgene was added dropwise thereto over a period of 5 minutes. After 20 minutes had elapsed therefrom, 0.20 g (2.0 mmol) of triethylamine was added dropwise thereto over 5 minutes, and the resulting mixture was then stirred for 30 minutes. The resulting reaction solution was poured into saturated sodium bicarbonate water, and was extracted with ethyl acetate. The organic layer was dried with magnesium sulfate, filtered and concentrated. The resulting crude product was purified by column chromatography (hexane/ethyl acetate) to obtain 2-t-butoxycarbonyl-2-para-nitrobenzoyl amino-6-chloromethyl pyridine which was the target product with a yield of 64% (as measured by HPLC).

Example B7

A solution C was obtained by dissolving 0.27 g (2.5 mmol) of triethylamine and 2.07 g (15 mmol) of triethylamine hydrochloride in 15 mL of chloroform.

A solution A was prepared by adding chloroform to 1.14 g (5.07 mmol) of 2-t-butoxycarbonyl amino-6-chloromethyl pyridine-N-oxide and 1.77 g (17.5 mmol) of triethylamine up to a total volume of 10 mL.

1.16 g (11.77 mmol) of phosgene was dissolved in chloroform and brought up to a total volume of 10 mL, thereby preparing a solution B.

The solution C was cooled to around −15° C. The solution A and solution B were added dropwise thereto at the same time over 40 minutes. After the completion of the dropwise addition, the reaction mixture was stirred for 30 minutes at −15° C. 10 mL of water was added to the aforementioned reaction mixture maintained at 0° C. or below. The pH was adjusted to 11 or more by adding an aqueous solution of caustic soda having a concentration of 28%. Following liquid separation, the resulting aqueous layer was extracted with chloroform. When the organic layer was quantitatively analyzed by HPLC, it was shown that 2-t-butoxycarbonyl amino-6-chloromethylpyridine which was the target product was obtained with a yield of 69%. 1% of byproducts (in terms of HPLC relative area percentage) was included therein.

Example B8

The reaction was carried out in the same manner as in Example B7 with the exception that triethylamine was replaced with di-1-propyl ethyl amine and triethylamine hydrochloride was replaced with di-1-propyl ethyl amine hydrochloride, respectively. The organic layer obtained by chloroform extraction was analyzed by HPLC. As a result, the byproduct content was 1% (HPLC relative area percentage). The organic layer was concentrated, and the resulting crude product was purified by silica gel column chromatography (hexane/ethyl acetate) to obtain 0.67 g of 2-t-butoxycarbonyl amino-6-chloromethyl pyridine (yield: 55%) which was the target product.

Example B9

20.37 g (92.2 mmol) of 2-t-butoxycarbonyl amino-6-methyl pyridine was dissolved in 100 mL of chloroform, and the resulting solution was cooled with ice water. 25 g (101.4 mmol) of a 70% by weight product of meta-chloroperbenzoic acid was added thereto. After confirming that there is no large heat generation, the temperature was raised to room temperature. After 2 hours had elapsed, 20 mL of water was added thereto. Then, the pH was adjusted to 14 by adding an aqueous solution of caustic soda having a concentration of 28%. Following liquid separation, the resulting aqueous layer was extracted with chloroform. The chloroform layer was washed with a 28% aqueous solution of caustic soda and then with water, and then dried with magnesium sulfate. Chloroform was removed by distillation under reduced pressure to obtain 21.30 g of 2-t-butoxycarbonyl amino-6-methyl pyridine-N-oxide (yield: 99.6%) in a light orange oily form.

The NMR spectrum and MS spectrum of the obtained 2-t-butoxycarbonyl amino-6-methyl pyridine-N-oxide were measured, and the following results were obtained.

$^1$H NMR: 1.53 (9H, s), 2.55 (3H, s), 6.87 (1H, d, J=7.6 Hz), 7.19 (1H, t, J=8.2 Hz), 8.01 (1H, d, J=8.8 Hz), 9.43 (1H, brs).

$^{13}$C NMR: 18.09, 28.01, 81.76, 110.23, 117.65, 126.68, 144.31, 146.85, 151.37.

MS m/z: 224 ($M^+$), 168, 151, 124, 107.

Example B10

4 mL of a chloroform solution containing 0.45 g (2 mmol) of 2-t-butoxycarbonyl amino-6-methyl pyridine-N-oxide and 0.26 g (2 mmol) of diisopropylethylamine was prepared, and was adjusted to 10° C. 0.29 g (2 mmol) of benzoyl chloride was added dropwise to the solution over 10 minutes at 10° C. After stirring further for 40 minutes at 10° C., 5 mL of water was added thereto, followed by liquid separation. The chloroform layer obtained by liquid separation was washed twice with 5 mL of water, and then dried with magnesium sulfate, followed by filtration. The resulting solution was concentrated under reduced pressure and dried to obtain 0.64 g of 2-t-butoxycarbonyl-2-benzoyl amino-6-methyl pyridine-N-oxide (yield: 97%) in the form of yellow-brown amorphous which was the target product.

The NMR spectrum of the obtained 2-t-butoxycarbonyl-2-benzoyl amino-6-methyl pyridine-N-oxide was measured, and the following results were obtained.

$^1$H-NMR: 1.23 (9H, s), 2.54 (3H, s), 7.20 (d, J=7.6 Hz, 1H), 7.23 (d, J=5.4 Hz, 1H), 7.35 (dd, J=7.6, 2.4 Hz, 1H), 7.44 (t, J=7.4 Hz, 2H), 7.53 (tt, J=7.4, 1.2 Hz, 1H), 7.92 (dd, J=6.8, 1.2 Hz, 2H).

$^{13}$C-NMR: 18.2, 27.5, 84.3, 123.4, 124.5, 124.8, 128.0, 128.7, 131.9, 135.6, 144.7, 149.2, 151.0, 170.9.

Example B11

2 mL of a chloroform solution containing 0.24 g (1 mmol) of 2-t-butoxycarbonyl amino-6-methyl pyridine and 0.26 g (2 mmol) of diisopropylethylamine was prepared, and was cooled in ice water. The above mixed solution was added dropwise at 0° C. to 0.3 mL of a chloroform solution containing 0.11 g (1.2 mmol) of methyl chloroformate. After stirring further for 20 minutes, the temperature was raised to room temperature. After stirring further for 5 hours at room temperature, 5 mL of water and 1 mL of 3N hydrochloric acid were added thereto, followed by liquid separation. The organic layer obtained by liquid separation was dried with magnesium sulfate, followed by filtration, and the resulting solution was concentrated under reduced pressure to obtain 0.27 g of 2-t-butoxycarbonyl-methoxycarbonyl amino-6-methyl pyridine-N-oxide (yield: 96%) as a pale yellow oily liquid which was the target product.

The NMR spectrum of the obtained 2-t-butoxycarbonyl-methoxycarbonyl amino-6-methyl pyridine-N-oxide was measured, and the following results were obtained.

$^1$H-NMR: 1.44 (9H, s), 2.54 (3H, s), 3.79 (3H, s), 7.13-7.26 (m, 3H).

Comparative Example B1

10 ml of a methylene chloride solution containing 1.99 g (6.7 mmol) of triphosgene was cooled to 0° C. 5 ml of a methylene chloride solution containing 1.12 g (5 mmol) of 2-t-butoxycarbonyl amino-6-methyl pyridine-N-oxide and 5 ml of a methylene chloride solution containing 1.01 g (10 mmol) of di-1-propylamine were each added dropwise thereto at the same time. After the completion of the dropwise addition, the liquid temperature was adjusted to room temperature, and the resulting mixture was then stirred for 1 hour. The reaction solution was poured into saturated sodium bicarbonate water, and was then extracted with methylene chloride. The organic layer was dried with magnesium sulfate, filtered and concentrated. The resulting crude product was purified by column chromatography (hexane/ethyl acetate). Only 73 mg of 2-t-butoxycarbonyl amino-6-chloromethyl pyridine which was the target product was obtained (yield: 3%). On the other hand, 503 mg (67%) of byproducts in the form of a white solid were produced.

Comparative Example B2

1.03 g (8 mmol) of di-1-propylethyl amine and 0.67 g (3 mmol) of 2-t-butoxycarbonyl amino-6-methyl pyridine-N-oxide were dissolved in 10 ml of methylene chloride, and the resulting solution was then cooled to −15° C. 20 mL of a methylene chloride solution containing 0.60 g (2 mmol) of triphosgene was added dropwise thereto over a period of 2 hours while maintaining the inner temperature at −15° C. After the completion of the dropwise addition, the resulting liquid was stirred for 1 hour at −15° C. 20 mL of water was added to the aforementioned reaction mixture maintained at 0° C. or below. The pH was adjusted to 11 or more by adding an aqueous solution of caustic soda having a concentration of 28%. Following liquid separation, the resulting aqueous layer was extracted with ethyl acetate. The organic layer was washed with water, dried with anhydrous magnesium sulfate, and then concentrated under reduced pressure. The resulting crude product was purified by silica gel column chromatography (hexane/ethyl acetate). 0.18 g of 2-t-butoxycarbonyl amino-6-chloromethyl pyridine which was the target product was obtained (yield: 25%). 4% of byproducts (in terms of HPLC relative area percentage) was produced.

Comparative Example B3

The reaction was carried out in the same manner as in Example B8 with the exception that no di-1-propyl ethyl amine hydrochloride was added. The yield of 2-t-butoxycarbonyl amino-6-chloromethyl pyridine after purification by silica gel column chromatography was 32%. 13% of byproducts (in terms of HPLC relative area percentage) was produced.

INDUSTRIAL APPLICABILITY

According to the production method of the present invention, nitrogen-containing heterocyclic compounds such as a substituted amino-6-methylpyridine-N-oxide derivative, and a haloalkyl, nitrogen-containing heterocyclic derivative can be obtained with high selectivity and also in high yield. The nitrogen-containing heterocyclic compound obtained by the production method of the present invention is useful as an intermediate for the industrial production of agricultural chemicals or the like.

The invention claimed is:

1. A method for producing a compound represented by formula (5) comprising reacting a compound represented by formula (4) with a halogenating agent:

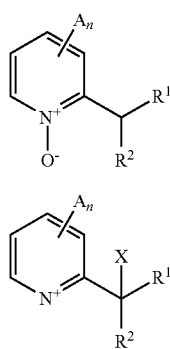

wherein
each of $R^1$ and $R^2$ independently represents a hydrogen atom, or an unsubstituted or substituted alkyl group, and $R^1$ and $R^2$ may form a ring together, A represents a hydroxyl group, a thiol group, an amino group, a nitro group, a halogen atom or an organic group, and at least one of A in formula (4) and formula (5) represents a group represented by formula(6):

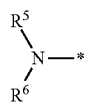

in formula (6), * indicates a binding site,
$R^5$ represents a hydrogen atom, an unsubstituted or substituted alkylcarbonyl group, an unsubstituted or substituted arylcarbonyl group, an unsubstituted or substituted heteroarylcarbonyl group, an unsubstituted or substituted alkoxycarbonyl group, an unsustituted or substituted arkylsulfonyl group, or an unsubstituted or substituted arylsulfonyl group, and
$R^6$ represents an unsubstituted or substituted alkylcarbonyl group, an unsubstituted or substituted arylcarbonyl group, an unsubstituted or substituted heteroarylcarbonyl group, an unsubtituted or substituted alkoxycarbonyl group, an unsubstituted or substituted alkylsulfonyl group, or an unsubtituted or substituted arylsulfonyl group, and $R^5$ and $R^6$ may be bonded to form a ring, n represents any one of integers of 1 to 4, and a plurality of A may be bonded to form a ring when n is 2 or more, and X represents a halogen atom.

2. The method according to claim 1, wherein the compound represented by formula (4) is a compound represented by formula (7), and the compound represented by formula (5) is a compound represented by formula (8):

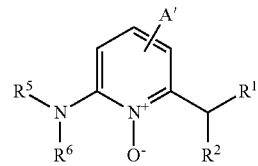

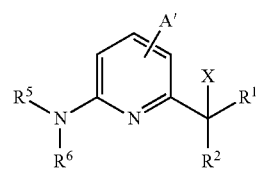

wherein $R^1$, $R^2$, $R^5$, and $R^6$ are the same as defined in claim 1,
A' represents a hydrohyl group, a thiol group, an amino group, a nitro group, a halogen atom or an organic group, and
l represents any one of integers of 0 to 3.

3. The method according to claim 1, wherein $R^5$ represents an unsubstituted or substituted alkylcarbonyl group, an unsubstituted or substituted arylcarbonyl group, or an unsubstituted or substituted alkoxycarbonyl group.

4. The method according to claim 1, wherein the halogenating agent is at least one selected from the group consisting of thionyl chloride, thionyl bromide, phosphorus oxychloride, sulfuryl chloride, phosgene, diphosgene and triphosgene.

5. The method according to claim 4, wherein the halogenating agent is at least one selected from the group consisting of thionyl chloride, thionyl bromide and sulfuryl chloride.

6. The method according to claim 4, wherein the halogenating agent is at least one selected from the group consisting of phosgene, diphosgene, triphosgene and phosphorus oxychloride.

7. The method according to claim 1, wherein the reaction is carried out in presence of a halogen ion source that is soluble in an organic solvent.

8. The method according to claim 7, wherein the halogen ion source that is soluble in an organic solvent is a halogenated ammonium salt or a halogenated phosphonium salt.

9. The method according to claim 7, wherein the halogen ion source that is soluble in an organic solvent is a tertiary or quaternary alkyl ammonium halide salt having an alkyl group of C2 or more, or an alkyl phosphonium halide salt having an alkyl group of C2 or more.

10. The method according to claim 8,
wherein the halogenating agent is at least one selected from the group consisting of thionyl chloride, thionyl bromide, phosphorus oxychloride, sulfuryl chloride, phosgene, diphosgene and triphosgene.

11. The method according to claim 9,
wherein the halogenating agent is at least one selected from the group consisting of thionyl chloride, thionyl bromide, phosphorus oxychloride, sulfuryl chloride, phosgene, diphosgene and triphosgene.

* * * * *